US012697200B2

(12) United States Patent
Casiraro et al.

(10) Patent No.: US 12,697,200 B2
(45) Date of Patent: Aug. 4, 2026

(54) VASCULAR IMPLANT

(71) Applicant: BARD PERIPHERAL VASCULAR, INC., Franklin Lakes, NJ (US)

(72) Inventors: Matt Casiraro, Tempe, AZ (US); Alexander Lastovich, Gilbert, AZ (US)

(73) Assignee: BARD PERIPHERAL VASCULAR, INC.

( * ) Notice: Subject to any disclaimer, the term of this patent is extended or adjusted under 35 U.S.C. 154(b) by 22 days.

(21) Appl. No.: 18/724,259

(22) PCT Filed: Dec. 30, 2021

(86) PCT No.: PCT/US2021/073177
§ 371 (c)(1),
(2) Date: Jun. 26, 2024

(87) PCT Pub. No.: WO2023/129177
PCT Pub. Date: Jul. 6, 2023

(65) Prior Publication Data
US 2025/0120801 A1      Apr. 17, 2025

(51) Int. Cl.
*A61F 2/01*            (2006.01)

(52) U.S. Cl.
CPC .......... *A61F 2/01* (2013.01); *A61F 2002/018* (2013.01); *A61F 2210/0004* (2013.01); *A61F 2220/0016* (2013.01); *A61F 2230/0008* (2013.01); *A61F 2240/001* (2013.01)

(58) Field of Classification Search
CPC ...... A61F 2/01; A61F 2/06; A61F 2/82; A61F 2/848; A61F 2002/018; A61F 2002/068;

A61F 2002/8483; A61F 2002/8486; A61F 2210/0004; A61F 2220/0016; A61F 2230/0008; A61F 2240/001

USPC ......................................................... 600/200
See application file for complete search history.

(56) References Cited

U.S. PATENT DOCUMENTS

| | | | |
|---|---|---|---|
| 8,092,484 B2 | 1/2012 | Kashkarov et al. | |
| 8,092,485 B2 | 1/2012 | Lapid | |
| 8,317,818 B2 | 11/2012 | Kashkarov et al. | |
| 8,420,113 B2 | 4/2013 | Zhao | |
| 8,518,072 B2 | 8/2013 | Miller | |
| 8,562,638 B2 | 10/2013 | Sokolov et al. | |

(Continued)

FOREIGN PATENT DOCUMENTS

| | | |
|---|---|---|
| EP | 2363156 A2 | 9/2011 |
| WO | 2007064731 A2 | 6/2007 |

(Continued)

OTHER PUBLICATIONS

Written Opinion of the International Searching Authority, PCT/US2021/73177, Sep. 20, 2022, 7 pages.

(Continued)

*Primary Examiner* — Kankindi Rwego
(74) *Attorney, Agent, or Firm* — Ballard Spahr LLP

(57) ABSTRACT

A vascular implant body having an oval shaped side wall surrounding a bore wherein the side wall has opposed curved end portions, an outer surface and an inner surface surrounding the bore. There are first and second filter openings on opposing ends of the bore. The body is sized and shaped to change the shape of the patient's vascular system at a vessel implant site and reduce the area available for emboli to pass.

20 Claims, 2 Drawing Sheets

(56) References Cited

U.S. PATENT DOCUMENTS

| | | | |
|---|---|---|---|
| 8,734,479 | B2 | 5/2014 | Kashkarov et al. |
| 8,777,975 | B2 | 7/2014 | Kashkarov et al. |
| 8,795,351 | B2 | 8/2014 | Weidman |
| 8,870,943 | B2 | 10/2014 | Nielsen |
| 8,992,562 | B2 | 3/2015 | Tessmer et al. |
| 9,220,588 | B2 | 12/2015 | Shinar et al. |
| 9,393,095 | B2 | 7/2016 | Miller |
| 9,421,081 | B2 | 8/2016 | Kashkarov et al. |
| 9,445,895 | B2 | 9/2016 | Kreidler |
| 9,456,888 | B2 | 10/2016 | Chin et al. |
| 9,468,513 | B2 | 10/2016 | Kashkarov et al. |
| 9,561,094 | B2 | 2/2017 | Fulton |
| 9,597,435 | B2 | 3/2017 | Edelman et al. |
| 9,693,851 | B2 | 7/2017 | Tessmer et al. |
| 9,730,781 | B2 | 8/2017 | Volobuyev et al. |
| 9,949,816 | B2 | 4/2018 | Becking et al. |
| 9,980,804 | B2 | 5/2018 | Harris et al. |
| 10,105,206 | B2 | 10/2018 | Simpson |
| 10,188,496 | B2 | 1/2019 | Chanduszko et al. |
| 10,188,498 | B2 | 1/2019 | Kashkarov et al. |
| 10,226,322 | B2 | 3/2019 | Miller |
| 10,258,454 | B2 | 4/2019 | Molgaard-Nielsen et al. |
| 10,279,078 | B2 | 5/2019 | Cox et al. |
| 10,299,906 | B2 | 5/2019 | Chanduszko et al. |
| 10,342,654 | B2 | 7/2019 | Chanduszko et al. |
| 10,368,972 | B2 | 8/2019 | Kashkarov et al. |
| 10,390,925 | B2 | 8/2019 | Weidman |
| 10,441,689 | B2 | 10/2019 | Weisman et al. |
| 10,470,865 | B2 | 11/2019 | Horan et al. |
| 10,492,898 | B2 | 12/2019 | Chanduszko et al. |
| 10,512,531 | B2 | 12/2019 | Tessmer et al. |
| 10,531,942 | B2 | 1/2020 | Eggers |
| 10,579,755 | B2 | 3/2020 | Greyf et al. |
| 10,624,731 | B2 | 4/2020 | Gilson et al. |
| 10,729,527 | B2 | 8/2020 | Carr, Jr. et al. |
| 10,813,738 | B2 | 10/2020 | Chanduszko et al. |
| 10,842,608 | B2 | 11/2020 | Harris et al. |
| 2002/0007222 | A1* | 1/2002 | Desai .......................... A61F 2/88 |
| | | | 623/23.65 |
| 2006/0015138 | A1 | 1/2006 | Gertner |
| 2007/0064731 | A1 | 3/2007 | Mizutani et al. |
| 2010/0074934 | A1 | 3/2010 | Hunter |
| 2015/0072293 | A1* | 3/2015 | DeSimone ............. B33Y 30/00 |
| | | | 355/18 |
| 2016/0166371 | A1 | 6/2016 | Johnson et al. |
| 2016/0175085 | A1 | 6/2016 | Johnson et al. |
| 2017/0105830 | A1 | 4/2017 | Klausen |
| 2017/0218228 | A1 | 8/2017 | Jose et al. |
| 2017/0249440 | A1 | 8/2017 | Lang et al. |
| 2017/0340429 | A1 | 11/2017 | Gilson et al. |
| 2018/0168811 | A1 | 6/2018 | Ranganathan et al. |
| 2018/0296343 | A1 | 10/2018 | Wei |
| 2018/0303616 | A1 | 10/2018 | Bhattacharyya et al. |
| 2018/0311028 | A1 | 11/2018 | Harris et al. |
| 2019/0110880 | A1 | 4/2019 | Fox et al. |
| 2020/0001540 | A1 | 1/2020 | McAlpine et al. |
| 2020/0197150 | A1 | 6/2020 | Gilson et al. |
| 2022/0008188 | A1* | 1/2022 | Karapetian ............... A61F 2/90 |

FOREIGN PATENT DOCUMENTS

| | | |
|---|---|---|
| WO | 2011079287 A1 | 6/2011 |
| WO | 2016154148 A1 | 9/2016 |
| WO | 2018117907 A1 | 6/2018 |
| WO | 2018218085 A2 | 11/2018 |
| WO | 2019178086 A1 | 9/2019 |
| WO | 2020123945 A1 | 6/2020 |

OTHER PUBLICATIONS

International Search Report, PCT/US2021/073177, Sep. 20, 2022, 6 pages.

* cited by examiner

VASCULAR IMPLANT

CROSS-REFERENCE TO RELATED APPLICATIONS

N/A

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to bioresorbable vascular implants such as filters (e.g., vena cava filters) and occlusion devices. More particularly, the present invention relates to a vascular implant that is sized and shaped to narrow and partially flatten the vessel where it is implanted (e.g., vena cava) to reduce the area available for emboli to pass. In one or more embodiments of the present invention, the improved vascular implant bioresorbs into a patient's vascular system (e.g., inferior vena cava, iliofemoral vein, ovarian veins, splenic artery, hepatic artery or other vein/artery vessel). For example, after transient risk of pulmonary embolism (PE) has subsided, the present invention bioresorbs into a patient's vascular system (e.g. inferior vena cava or iliofemoral vein). The entire implant structure could be made of bioresorbable material so that no implant or implant remnant/element would ultimately be left behind as the entire implant would resorb into vascular tissue.

2. General Background of the Invention

Vascular implants include various devices that are placed at a selected locale in a patient's blood vessel. One example is a vena cava filter. Another example is an occlusion device. Various patents have issued for vascular implants. Patents have also issued that relate in general to 3D printing of implants. Examples are listed in the following Table 1. Each patent listed in Table 1 is hereby incorporated herein by reference.

TABLE 1

| PATENT OR PUBLICATION NO. | TITLE | ISSUE DATE (DD/MM/YYYY) |
|---|---|---|
| 8,092,484 | EMBOLUS BLOOD CLOT FILTER WITH POST DELIVERY ACTUATION | 10 Jan. 2012 |
| 8,092,485 | RECOVERABLE INFERIOR VENA CAVA FILTER | 10 Jan. 2012 |
| 8,317,818 | REMOVABLE BLOOD CLOT FILTER WITH EDGE FOR CUTTING THROUGH THE ENDOTHELIUM | 27 Nov. 2012 |
| 8,420,113 | BIODEGRADABLE MEDICAL DEVICES WITH ENHANCED MECHANICAL STRENGTH AND PHARMACOLOGICAL FUNCTIONS | 16 Apr. 2013 |
| 8,518,072 | JUGULAR FEMORAL VENA CAVA FILTER SYSTEM | 27 Aug. 2013 |
| 8,562,638 | EMBOLUS BLOOD CLOT FILTER WITH FLOATING FILTER BASKET | 22 Oct. 2013 |

TABLE 1-continued

| PATENT OR PUBLICATION NO. | TITLE | ISSUE DATE (DD/MM/YYYY) |
|---|---|---|
| 8,734,479 | EMBOLUS BLOOD CLOT FILTER DELIVERY SYSTEM | 27 May 2014 |
| 8,777,975 | EMBOLUS BLOOD CLOT FILTER WITH BIO-RESORBABLE COATED FILTER MEMBERS | 15 Jul. 2014 |
| 8,795,351 | MIGRATION RESISTANT EMBOLIC FILTER | 5 Aug. 2014 |
| 8,870,943 | STENT STRUCTURE FOR IMPLANTATBLE MEDICAL DEVICE | 28 Oct. 2014 |
| 8,992,562 | FILTER DELIVERY SYSTEM | 31 Mar. 2015 |
| 9,220,588 | SYSTEMS, METHODS AND DEVICE FOR EMBOLIC PROTECTION | 29 Dec. 2015 |
| 9,393,095 | JUGULAR FEMORAL VENA CAVA FILTER SYSTEM | 19 Jul. 2016 |
| 9,421,081 | EMBOLUS BLOOD CLOT FILTER DELIVERY SYSTEM | 23 Aug. 2016 |
| 9,445,895 | INTRACARDIAC CAGE AND METHOD OF DELIVERING SAME | 25 Sep. 2016 |
| 9,456,888 | REVERSIBLE VASCULAR FILTER DEVICES AND METHODS | 4 Oct. 2016 |
| 9,468,513 | EMBOLUS BLOOD CLOT FILTER WITH BIO-RESORBABLE COATED FILTER MEMBERS | 18 Oct. 2016 |
| 9,561,094 | DEVICES AND METHODS FOR TREATING VENOUS DISEASES | 7 Feb. 2017 |
| 9,597,435 | MEDICAL DEVICES HAVING A BIORESORBABLE COATING LAYER WITH A PRE-DETERMINED PATTERN FOR FRAGMENTATION | 21 Mar. 2017 |
| 9,693,851 | FILTER DELIVERY SYSTEM | 14 Jul. 2017 |
| 9,730,781 | EMBOLUS BLOOD CLOT FILTER REMOVAL SYSTEM AND METHOD | 15 Aug. 2017 |
| 9,949,816 | IVE FILTER RETRIEVAL SYSTEMS WITH MULTIPLE CAPTURE MODES | 24 Apr. 2018 |
| 9,980,804 | VENA CAVA FILTER WITH FILAMENT | 29 May 2018 |
| 10,105,206 | INFERIOR VENA CAVA FILTER WITH STABILITY FEATURES | 23 Oct. 2018 |
| 10,188,496 | VENA CAVA FILTER FORMED FROM A SHEET | 29 Jan. 2019 |
| 10,188,498 | EMBOLUS BLOOD CLOT FILTER DELIVERY SYSTEM | 29 Jan .2019 |
| 10,226,322 | JUGULAR FEMORAL VENA CAVA FILTER SYSTEM | 12 Mar. 2019 |
| 10,258,454 | VISUAL STABILIZER ON ANCHOR LEGS OF VENA CAVA FILTER | 16 Apr. 2019 |
| 10,279,078 | CROSSLINKABLE 3D PRINTED BIOMATERIAL-BASED IMPLANTS AND METHODS OF MANUFACTURE THEREOF | 7 May 2019 |
| 10,299,906 | EMBOLUS BLOOD CLOT FILTER UTILIZABLE WITH SINGLE DELIVERY SYSTEM OR A SINGLE RETRIEVAL SYSTEN IN ONE OF A FEMORAL OR JUGULAR ACCESS | 28 May 2019 |
| 10,342,654 | IVC FILTER WITH TRANSLATING HOOKS | 9 Jul. 2019 |
| 10,368,972 | EMBOLUS BLOOD CLOT FILTER WITH BIO-RESORBABLE COATED FILTER MEMBERS | 6 Aug. 2019 |
| 10,390,925 | MIGRATION RESISTANT EMBOLIC FILTER | 27 Aug. 2019 |
| 10,441,689 | METHODS AND DEVICES FOR THREE-DIMENSIONAL PRINTING OR ADDITIVE MANUFACTURING OF BIOACTIVE MEDICAL DEVICES | 15 Oct. 2019 |
| 10,470,865 | VASCULAR FILTER DEVICE | 12 Nov. 2019 |
| 10,492,898 | EMBOLUS BLOOD CLOT FILTER AND DELIVERY SYSTEM | 3 Dec. 2019 |
| 10,512,531 | FILTER DELIVERY SYSTEM | 24 Dec. 2019 |
| 10,531,942 | ABSORBABLE VASCULAR FILTER | 14 Jan. 2020 |
| 10,579,755 | METHOD FOR 3-DAY PRINTING A CUSTOM BONE GRAFT | 3 Mar. 2020 |
| 10,624,731 | VASCULAR FILTER SYSTEM | 21 Apr. 2020 |
| 10,729,527 | REMOVABLE EMBOLUS BLOOD CLOT FILTER | 4 Aug. 2020 |

TABLE 1-continued

| PATENT OR PUBLICATION NO. | TITLE | ISSUE DATE (DD/MM/YYYY) |
|---|---|---|
| 10,813,738 | TUBULAR FILTER | 27 Oct. 2020 |
| 10,842,608 | VENA CAVA FILTER WITH FILAMENT | 24 Nov. 2020 |
| 2007/064731 | TRANSMISSION APPARATUS WITH FUNCTION OF MULTI-STEP BANDWIDTH ASSIGNMENT TO OTHER COMMUNICATION APPARATUSES | 22 Mar. 2007 |
| 2010/0074934 | MEDICAL IMPLANTS WITH A COMBINATION OF COMPOUNDS | 25 Mar. 2010 |
| 2016/0166371 | ENDOLUMINAL FILTER DESIGN VARIATIONS | 16 Jun. 2016 |
| 2016/0175085 | ENHANCED FLUOROGENIC ENDOLUMINAL FILTER STRUCTURE | 23 Jun. 2016 |
| 2017/0105830 | BIODEGRADABLE VASCULAR FILTER | 20 Apr. 2017 |
| 2017/0218228 | THREE DIMENSIONAL PRINTING OF BIO-INK COMPOSITIONS | 3 Aug. 2017 |
| 2017/0249440 | 3D PRINTING SURGICAL REPAIR SYSTEMS | 31 Aug. 2017 |
| 2017/0340429 | VASCULAR FILTER SYSTEM | 30 Nov. 2017 |
| 2018/0168811 | NOVEL BIODEGRADABLE AND NON-BIODEGRADABLE 3D PRINTED IMPLANTS AS A DRUG DELIVERY SYSTEM | 21 Jun. 2018 |
| 2018/0296343 | 3-D PRINTING OF POROUS IMPLANTS | 18 Oct. 2018 |
| 2018/0303616 | 3-D PRINTING OF BONE GRAFTS | 25 Oct. 2018 |
| 2018/0311028 | VENA CAVA FILTER WITH FILAMENT | 1 Nov. 2018 |
| 2019/0110880 | MEDICAL DEVICES AND ANCHORS THREFOR | 18 Apr. 2020 |
| 2020/0001540 | ADDITIVE MANUFACTURING ON UNCONSTRAINED FREEDOM SURFACES | 2 Jan. 2020 |
| 2020/0197150 | VASCULAR FILTER SYSTEM | 25 Jun. 2020 |
| WO2007064731 | HELICAL VENA CAVA FILTER | 7 Jun. 2007 |
| WO2011079287 | REVERSIBLE VASCULAR FILTER DEVCIES AND METHODS FOR USING SAME | 30 Jun. 2011 |
| WO2016154148 | ARTIFICIAL TYMPANIC MEMBRANE DEVICES AND USES | 29 Sep. 2016 |
| WO2018117907 | SHAPE MEMORY POLYMER COMPOSITE FOR 3D PRINTING OF MEDICAL ITEMS | 28 Jun. 2018 |
| WO2018218085 | THREE-DIMENSIONAL PRINTED ORGANS, DEVICES, AND MATRICES | 29 Nov. 2018 |
| WO2019178086 | ELECTROHYDRODYNAMIC BIOPRINTER SYSTEM AND METHOD | 19 Sep. 2019 |
| WO2020123945 | FABRIC MATERIAL FOR MEDICAL DEVICES | 18 Jun. 2020 |
| EP2363156 | METHOD OF FABRICATING BIODEGRADABLE MEDICAL DEVICES WITH ENHANCED MECHANICAL STRENGTH AND PHARMACOLGOICAL FUNCTIONS | 7 Sep. 2011 |

BRIEF SUMMARY OF THE INVENTION

The present invention provides a vascular implant preferably having an oval shaped side wall surrounding a bore wherein the side wall has opposed curved end portions, an outer surface and an inner surface surrounding the bore.

In one or more embodiments, there are preferably first and second filter openings on opposing ends of the bore.

In one or more embodiments, the body is preferably sized and shaped to change the shape of the patient's vascular system at a vessel implant site and reduce the area available for emboli to pass.

In one or more embodiments, the filter body is preferably 3D printed of a polymeric material.

In one or more embodiments, the implant body is preferably of a bioresorbable material.

In one or more embodiments, there are preferably one or more anchors on the side wall outer surface.

In one or more embodiments, the anchors are preferably on said curved end portions.

In one or more embodiments, the anchors preferably include proximal and distal anchors.

In one or more embodiments, there are at least a pair of anchors on each curved end portion.

In one or more embodiments, the implant body has proximal and distal edges, at least one anchor next to the proximal edge and at least one anchor next to the distal edge.

In one or more embodiments, at least a portion of the side wall is flat.

In one or more embodiments, the side wall has elongated or planar sections that each connect to a curved end position.

In one or more embodiments, the implant body has an oval shaped side wall surrounding a bore wherein the side wall has opposed curved end portions, an outer surface and an inner surface surrounding the bore.

In one or more embodiments, the body is sized and shaped to change the shape of the patient's vascular system at a vessel implant site in order to reduce the area available for emboli to pass.

In one or more embodiments, the body is rigid enough to change the shape of the vessel where the implant body is placed.

In one or more embodiments, the filter body is 3D printed of a polymeric material.

In one or more embodiments, the implant body is of a bioresorbable material.

In one or more embodiments, the anchors are preferably on the curved end portions.

In one or more embodiments, the implant body is of a bioresorbable polymer.

In one or more embodiments, the side wall has elongated or planar sections that each connect to the curved end position.

In one or more embodiments, the side wall preferably has one or more corrugated portions.

In one or more embodiments, there are preferably two (2) opposed corrugated portions.

In one or more embodiments, an elongated implant body has a length and a width, a wall that includes first and second opposed curved end portions, and opposed elongated wall sections that each connect to the first and second opposed curved end portions, the length is preferably greater than said width, and the wall preferably has an inner surface surrounding an open ended bore.

In one or more embodiments, there are preferably openings on opposing ends of the bore.

In one or more embodiments, the body is sized and shaped to change the shape of the patient's vascular system at a vessel implant site and reduce the area available for emboli to pass.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
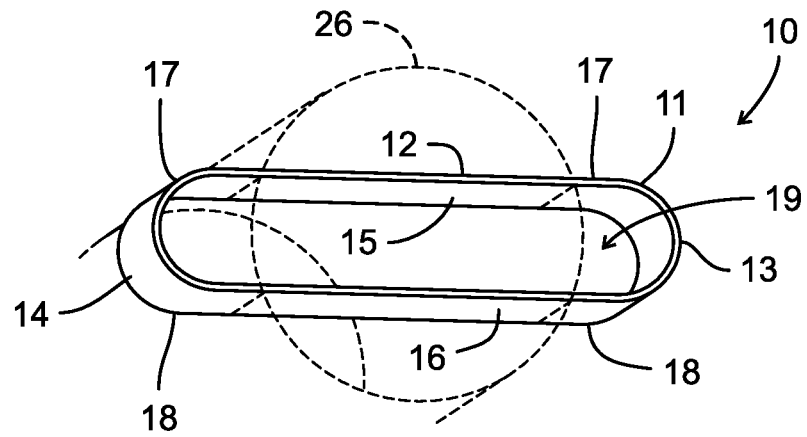
FIG. 1 is a perspective view of a preferred embodiment of the apparatus of the present invention.
Figure 2:
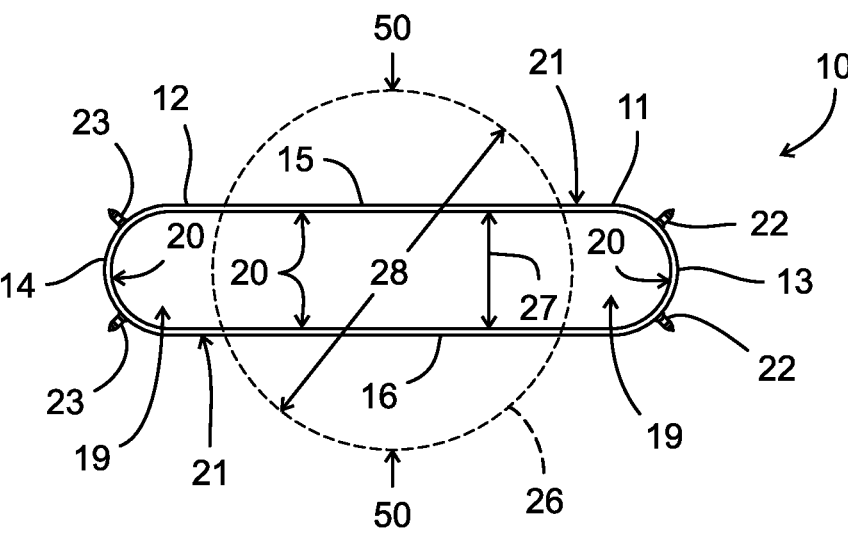
FIG. 2 is a top view of a preferred embodiment of the apparatus of the present invention.
Figure 3:
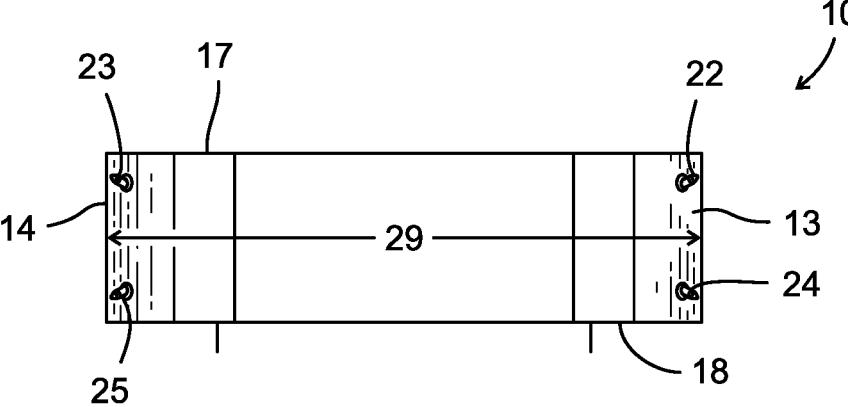
FIG. 3 is a side view of a preferred embodiment of the apparatus of the present invention.

FIGS. 1-3 show a first embodiment of the apparatus of the present invention, designated generally by the numeral 10. Vascular implant 10 has an implant body 11. The implant body can be 3D printed of a polymeric material. The implant body can be of a bioresorbable material. In a currently preferred embodiment, the implant body 11 can be of polymeric resorbable material.

The implant 10 could be deployed with either a femoral or jugular approach. Such a deployment could employ a pusher or pusher apparatus/mechanism such as one specified in one or more of the patents listed in Table 1. An example is U.S. Pat. No. 8,518,072 naming Jonathan Miller as inventor and assigned to C. R. Bard, Inc. Implant 10 could also be a balloon-mounted implant that is then expanded with balloon dilation, as seen, for example, in balloon expandable stents. Once implanted inside a selected vessel 26 or vascular location, the shape of the implant body 11 causes the vessel 26 to partially flatten as the selected vessel assumes the shape of the implant body 11 (as shown by the arrows 50 in FIG. 2). This prevents emboli from passing, in the direction of blood flow beyond the location of the implant with a simple type of implant. Additionally but not necessarily, the implant may be such that the flow profile in the flattened vessel is not disturbed thereby, and the implant does contain parts which project into the center of the vessel. Thereby the risk of complications can be reduced.

In this embodiment, the implant body has first and second filter openings, and a length and a width in a plane transverse to the direction of blood flow, from the first filter to the second filter opening or vice versa. The length 29 is greater than the width 27. When the implant is placed, the longitudinal end portions 13, 14 push the vessel outwards in the regions of contact between the longitudinal end portions 13, 14 and the vessel, and the vessel is deformed thereby such that the implant fits inside the vessel. At the same time, due to this deformation the vessel will be flattened in the transverse direction of the elongated shape, thus reducing the available area or dimension for emboli to pass (see FIG. 2). Vessel 26 is deformed to and conforms to the shape of body 11 and widened in the longitudinal direction while narrowed in the transverse direction.

In the shown embodiment, the body 11 comprises a wall 12 that includes first and second opposed curved end portions 13, 14 and opposed elongated wall sections 15, 16 that each connect to the first and second opposed curved end portions. The wall 12 has an inner surface 20 surrounding an open ended bore 19, with the first and second filter openings on opposing ends of the bore. The side wall 12 can be shaped as an open cylinder with an elongated base, and in this embodiment has an oval base. The side wall 12 extends between the first and second filter openings. In this example, the height of the cylinder, that is the distance between the opposing ends of the bore 19, is about the same as the width of the elongated base thereof. This facilitates manipulation of the body inside the vessel.

In an embodiment, the flow resistance of the bore 19 is the same as the flow resistance of the vessel over the distance where the bore is placed. Thereby the risk of complications after placing the implant can be reduced.

The bore 19 has a generally oval or elongated shaped cross-section perpendicular to the axial direction of the implant body. This allows to reduce the changes in flow profile of the vessel caused by placing the implant 10. The implant body 11 can be placed inside the vessel with the axis of the bore 19 parallel to the direction of blood flow, and the sidewall 12 parallel to the vessel. The length of the oval or elongated shape, in case of an ellipse this is the distance between the vertex points of the major axis, is larger than the diameter 28 of vessel 26. Vessel 26 thus conforms to the generally oval or elongated shape of body 11. The width 27 of implant body 11 is smaller than the diameter 28 of vessel 26, thus reducing the available area or dimension for emboli to pass (see FIG. 2).

The circumference of the implant body 11 can be equal to the circumference of the vessel, in which case the vessel effectively fits around the implant body 11 without being stretched. The circumference of the implant body 11 can be larger than the circumference of the vessel, in which case the vessel effectively fits around the implant body 11 while being stretched to make the circumferences equal, which may allow for a frictional anchoring. The circumference of the implant body 11 can be smaller than the circumference of the vessel, in which case at some locations a passage may remain between vessel and the implant body 11 through which blood can flow, but of which passage the available area or dimension for emboli to pass is reduced.

In case the implant body 11 is of a bioresorbable material, due to the proximity, and in this example the contact, of the wall to the vessel, the implant body 11 will over time be resorbed into the vessel. When of a bioresorbable material, the bioresorption starts as soon as the implant is exposed to the blood and like many of the standard polymers degrades over time via polymer breakdown and absorption of the byproducts. This bioresorption can be tuned as needed to ensure the implant maintains structural filtering integrity until transient risk of pulmonary embolism has subsided. Thereby, the need for a retrieval procedure on the patient to retrieve the implant can be obviated. In an embodiment, the implant body 11 adheres to the vessel, such that when the implant body 11 is not homogeneously resorbed and e.g. breaks, the separate parts remain in position.

In one or more embodiments, implant body 11 can be placed in a vessel such as the vena cava. In such a case, width or diameter 27 of body 11 can be between about 15 and 30 mm for inferior vena cava pulmonary embolism prevention. For iliofemoral prevention, the implant 10 body 11 can have a width or diameter of between about 6 and 20 mm. For other smaller vessels, the diameter or width can be between about 2 and 8 mm. Length 29 of body 11 (see FIG. 3) can preferably be between about 5 and 50 mm. It is currently believed that such dimensions provide an effective filtering with less risk of damage to the vessel.

Implant body 11 has side wall 12 that includes curved end portions 13, 14 and planar or elongated sections 15, 16 (see FIG. 2). This allows to reduce complications caused by placing the implant body since the shape of the implant body 11 is smooth and the risk of damage to the vessel can be reduced. Side wall 12 has inner surface 20 and outer surface 21. When placed in the vessel, the outer surface 21 abuts and contacts the vessel, and blood flows through the open-ended bore or passageway 19, with non-circular cross-section, defined by the inner surface 20. Implant body 11 has proximal edge 17 and distal edge 18. In this embodiment, the first and second filter openings are located at a respective edge 17, 18. Open ended bore or passage 19 extends from edge 17 to edge 18 (see FIG. 3). Anchors are provided to anchor implant body 11 to a vessel wall or other vascular site. In this example, the anchors are located on the outer surface 21. The anchors project from the outer surface 21, and when the implant body 11 is placed, the anchors project into the wall of the vessel. Anchors include proximal anchor or anchors 22 at curved end portion 13 and proximal anchor or anchors 23 at curved end portion 14. Distal anchors can include distal anchor or anchors 24 at curved end portion 13 and distal anchor or anchors 25 at curved end portion 14 (see FIG. 3).

Figure 4:
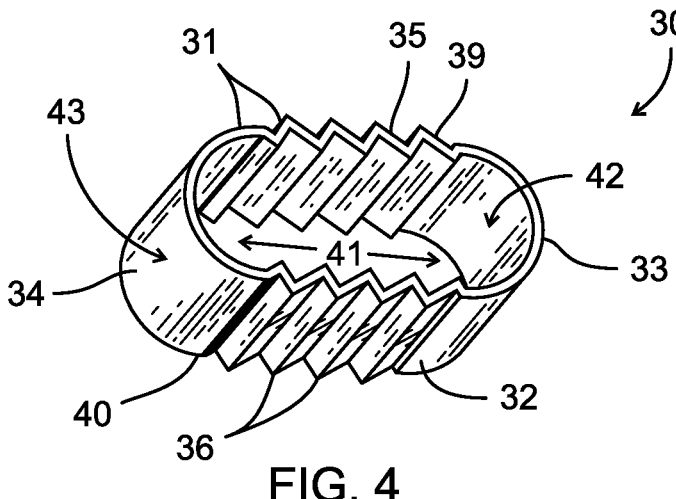
FIG. 4 is a perspective view of a second embodiment of the apparatus of the present invention.
Figure 5:
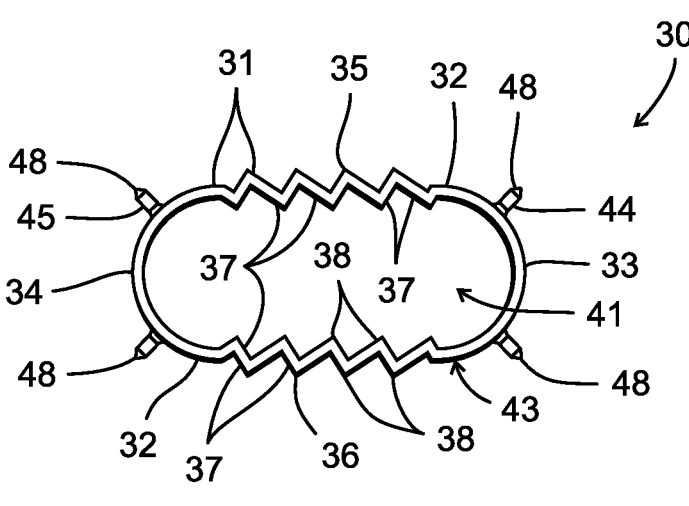
FIG. 5 is a top view of a second embodiment of the apparatus of the present invention.
Figure 6:
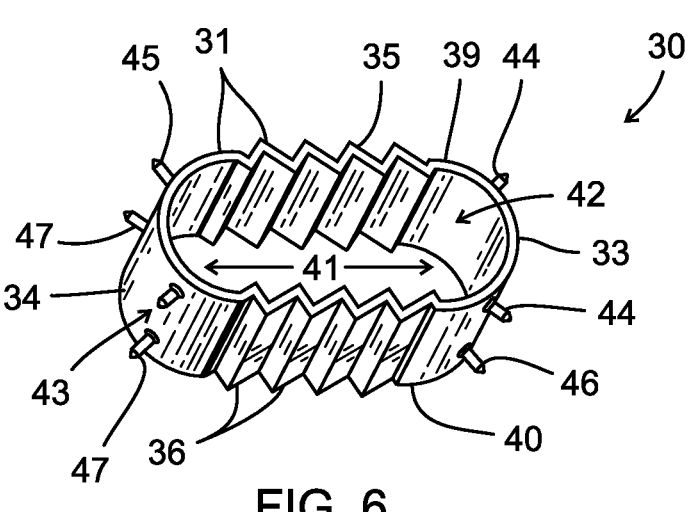
FIG. 6 is a perspective view of a second embodiment of the apparatus of the present invention.

FIGS. 4-6 show a second embodiment, designated by the numeral 30. Vascular implant 30 is similar to vascular implant 10 but has corrugated portions 35, 36 instead of the straight, planar or elongated sections 15, 16. Vascular implant 30 has an implant body 31 with side wall 32. Implant body 31 has curved end portions 33, 34 that each connect to corrugated portions 35, 36 as seen in FIGS. 4-6.

Each corrugated portion can include multiple panels 37 joined at intersections 38 as shown. Implant body 31 has proximal edge 39 and distal edge 40 (see FIGS. 4, 6). Implant body 31 has an open ended bore or passageway 41. Side wall 32 has inner surface 42 and outer surface 43. As with the embodiment of FIGS. 1-3, anchors can be provided on outer surface 43 including proximal anchors 44 and distal anchors 46 at curved end 33 (see FIG. 6). Proximal anchors 45 and distal anchors 47 can be provided at curved end portion 34. Anchors 44-47 can each have a sharpened tip 48 that aids in penetrating vascular tissue at a selected implant site.

The vascular implant can thus be characterized by comprising an elongated implant body having a length and a width and being sized and shaped to change the shape of the patient's vascular system at a vessel implant site and reduce the area available for emboli to pass.

Without limitation, the implant may further be characterized by comprising a wall that includes first and second opposed curved end portions and opposed elongated wall sections that each connect to the first and second opposed curved end portions, the length greater than the width, the wall having an inner surface surrounding an open-ended bore, and first and second filter openings on opposing ends of the bore.

Without limitation, the implant may further be characterized by one or more of the following statements:

Statement 1: A vascular implant, comprising:
a) an implant body comprising an oval shaped side wall surrounding a bore wherein the side wall includes opposed curved end portions, an outer surface and an inner surface surrounding the bore;
b) first and second filter openings on opposing ends of the bore;
c) wherein the body is sized and shaped to change the shape of the patient's vascular system at a vessel implant site and reduce the area available for emboli to pass.

Statement 2: The vascular implant of statement 1 wherein the implant body is 3D printed of a polymeric material.

Statement 3: The vascular implant of one or more of the preceding statements wherein the implant body is of a bioresorbable material.

Statement 4: The vascular implant of one or more of the preceding statements further comprising one or more anchors on the side wall outer surface.

Statement 5: The vascular implant of statement 4 wherein the anchors are on the curved end portions.

Statement 6: The vascular implant of statement 4 or 5 wherein the anchors include proximal and distal anchors.

Statement 7: The vascular implant of one or more of statements 4-6 wherein there are at least a pair of the anchors on each the curved end portion.

Statement 8: The vascular implant of one or more of statements 4-7 wherein the implant body has proximal and distal edges, at least one the anchor next to the proximal edge and at least one the anchor next to the distal edge.

Statement 9: The vascular implant of one or more of the preceding statements wherein at least a portion of the side wall is flat.

Statement 10: The vascular implant of one or more of the preceding statements wherein the side wall has elongated or planar sections that each connect to a curved end position.

Statement 11: A vascular implant, comprising:
a) an implant body comprising an oval shaped side wall surrounding a bore wherein the side wall has opposed curved end portions, an outer surface and an inner surface surrounding the bore;
b) wherein the body is sized and shaped to change the shape of the patient's vascular system at a vessel implant site in order to reduce the area available for emboli to pass; and
c) wherein the implant body is rigid enough to change the shape of the vessel where the implant body is placed.

Statement 12: The vascular implant of statement 11 wherein the implant body is 3D printed of a polymeric material.

Statement 13: The vascular implant of statement 11 or 12 wherein the implant body is of a bioresorbable material.

Statement 14: The vascular implant of one or more of statements 11-13 further comprising one or more anchors on the side wall outer surface.

Statement 15: The vascular implant of one or more of statements 11-14 wherein the anchors are on the curved end portions.

Statement 16 The vascular implant of one or more of statements 11-15 wherein the implant body is of a bioresorbable polymeric material.

Statement 17: The vascular implant of one or more of statements 11-16 wherein the side wall has elongated or planar sections that each connect to a the curved end position.

Statement 18: The vascular implant of one or more of statements 11-17 wherein the side wall has one or more corrugated portions.

Statement 19: The vascular implant of statement 18 wherein there are two (2) opposed corrugated portions.

The following is a list of parts and materials suitable for use in the present invention.

PARTS LIST

| Part Number | Description |
| --- | --- |
| 10 | vascular implant |
| 11 | implant body |
| 12 | side wall |
| 13 | curved end portion |
| 14 | curved end portion |
| 15 | planar section/elongated section |
| 16 | planar section/elongated section |
| 17 | proximal edge |
| 18 | distal edge |
| 19 | open ended bore/passage |

9

-continued

| Part Number | Description |
| --- | --- |
| 20 | side wall inner surface |
| 21 | side wall outer surface |
| 22 | proximal anchor |
| 23 | proximal anchor |
| 24 | distal anchor |
| 25 | distal anchor |
| 26 | vessel/vascular tissue/vascular location |
| 27 | width |
| 28 | diameter |
| 29 | length |
| 30 | vascular implant |
| 31 | implant body |
| 32 | side wall |
| 33 | curved end portion |
| 34 | curved end portion |
| 35 | corrugated portion |
| 36 | corrugated portion |
| 37 | panel |
| 38 | intersection |
| 39 | proximal edge |
| 40 | distal edge |
| 41 | open ended bore/passageway |
| 42 | side wall inner surface |
| 43 | side wall outer surface |
| 44 | proximal anchor |
| 45 | proximal anchor |
| 46 | distal anchor |
| 47 | distal anchor |
| 48 | sharp tip |
| 50 | arrow |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A vascular implant, comprising:
a) an implant body having an oval shaped side wall surrounding a bore wherein said side wall includes opposed curved end portions, an outer surface and an inner surface surrounding said bore;
b) first and second filter openings on opposing ends of said bore;
c) wherein said body is sized and shaped to change a shape of a patient's vascular system at a vessel implant site and reduce an area available for emboli to pass; and
d) wherein, after placement in the vessel implant site, the body is configured to maintain a shape thereof until the vascular implant is retrieved, reabsorbed, or breaks.

2. The vascular implant of claim 1 wherein said implant body is 3D printed of a polymeric material.

3. The vascular implant of claim 1 wherein the implant body is of a bioresorbable material.

4. The vascular implant of claim 1 further comprising one or more anchors on said side wall outer surface.

5. The vascular implant of claim 4 wherein said anchors are on said curved end portions.

6. The vascular implant of claim 4 wherein said anchors include proximal and distal anchors.

7. The vascular implant of claim 4 wherein there are at least a pair of said anchors on each said curved end portion.

8. The vascular implant of claim 5 wherein said implant body has proximal and distal edges, at least one said anchor next to said proximal edge and at least one said anchor next to said distal edge.

9. The vascular implant of claim 1 wherein at least a portion of said side wall is flat.

10. The vascular implant of claim 1 wherein said side wall has elongated or planar sections that each connect to a said curved end position.

11. A vascular implant, comprising:
a) an implant body having an oval shaped side wall surrounding a bore wherein said side wall has opposed curved end portions, an outer surface and an inner surface surrounding said bore;
b) wherein said body is sized and shaped to change a shape of a patient's vascular system at a vessel implant site in order to reduce an area available for emboli to pass; and
c) wherein said implant body is rigid enough to change the shape of the vessel where said implant body is placed; and
d) wherein, after placement in the vessel implant site, the body is configured to maintain a shape thereof until the vascular implant is retrieved, reabsorbed, or breaks.

12. The vascular implant of claim 11 wherein said implant body is 3D printed of a polymeric material.

13. The vascular implant of claim 11 wherein the implant body is of a bioresorbable material.

14. The vascular implant of claim 11 further comprising one or more anchors on said side wall outer surface.

15. The vascular implant of claim 11 wherein said anchors are on said curved end portions.

16. The vascular implant of claim 11 wherein the implant body is of a bioresorbable polymeric material.

17. The vascular implant of claim 11 wherein said side wall has elongated or planar sections that each connect to a said curved end position.

18. The vascular implant of claim 11 wherein said side wall has one or more corrugated portions.

19. The vascular implant of claim 18 wherein there are two (2) opposed corrugated portions.

20. A vascular implant, comprising:
a) an elongated implant body having a length and a width, a wall that includes first and second opposed curved end portions and opposed elongated wall sections that each connect to said first and second opposed curved end portions, said length greater than said width, said wall having an inner surface surrounding an open ended bore;
b) first and second filter openings on opposing ends of said bore; and
c) wherein said body is sized and shaped to change a shape of a patient's vascular system at a vessel implant site; and
d) wherein the body is configured to prevent an emboli from passing through the vessel implant site at least until emboli risk has subsided.

* * * * *